United States Patent [19]

Desmurs et al.

[11] Patent Number: 5,149,858

[45] Date of Patent: Sep. 22, 1992

[54] SELECTIVE ORTHO-CHLORINATION OF PHENOLS

[75] Inventors: Jean-Roger Desmurs, Saint-Symphorien D'Ozon; Bernard Besson, Pont De Claix; Isabelle Jouve, Villeubanne, all of France

[73] Assignee: Rhone-Poulenc Chimie, Courbevoie, France

[21] Appl. No.: 219,780

[22] Filed: Jul. 18, 1988

[30] Foreign Application Priority Data

Jul. 17, 1987 [FR] France .................. 87 10418

[51] Int. Cl.⁵ ............... C07C 253/30; C07C 37/62
[52] U.S. Cl. ..................... 558/419; 558/423; 568/645; 568/765; 568/775; 568/779
[58] Field of Search ........... 558/423, 419; 568/779, 568/765, 775, 645

[56] References Cited

U.S. PATENT DOCUMENTS 4,160,114  7/1979  Shelton et al. .................. 568/776
4,620,042  10/1986  Kawai et al. ..................... 568/779

FOREIGN PATENT DOCUMENTS 72514  2/1983  European Pat. Off. .......... 568/779
196260  10/1986  European Pat. Off. .......... 568/779
61-207351  9/1986  Japan .
1207351  9/1986  Japan ............................. 568/779

OTHER PUBLICATIONS

Chemical Abstracts vol. 72, No. 15, Abst. No. 78573v.

*Primary Examiner*—Joseph Paul Brust
*Assistant Examiner*—Jacqueline Haley
*Attorney, Agent, or Firm*—Burns, Doane, Swecker & Mathis

[57] ABSTRACT

Phenolic compounds, notably admixtures of 2,4-dichlorophenol and 2,6-dichlorophenol, are selectively chlorinated at the ortho positions thereof, with gaseous chlorine and in a molten medium, in the presence of a selectivity-enhancing effective amount of an organic cation.

13 Claims, No Drawings

SELECTIVE ORTHO-CHLORINATION OF PHENOLS

CROSS-REFERENCE TO COMPANION APPLICATIONS

Our copending applications, Serial No. 220,729 and U.S. Pat. application Ser. No. 220,254 both filed concurrently herewith and both assigned to the assignee hereof.

BACKGROUND OF THE INVENTION

1. Field of the Invention

The present invention relates to the selective chlorination of phenolic compounds, in the ortho position relative to the hydroxyl group, using gaseous chlorine.

2. Description of the Prior Art

In the preparation of chlorophenols by chlorination of phenol, isomers are obtained at the various reaction stages, and this ultimately gives rise to numerous compounds which must subsequently be separated by means of costly and difficult purification techniques. On the other hand, the ratios of the various isomers obtained do not automatically correspond to that which would be economically worthwhile, given the existing markets.

Need therefore exists for processes enabling a selective chlorination, especially for a selective chlorination in the ortho position or in the para position relative to the hydroxyl group of the phenolic compound.

Thus, published German Patent Application No. 3,318,791 describes a process for the selective chlorination of phenol to give 2-chlorophenol, in a perchlorinated apolar solvent and in the presence of a branched-chain amine.

However, the use of a solvent in an industrial scale chlorination process may, in certain cases, present disadvantages, such as, for example, the requirement for a larger reactor volume and a more difficult separation of the reaction products.

Cf. U.S. Pat. No. 4,160,114, Patent Abstracts of Japan, 11, No. 43 (C-402) [2490], Feb. 7, 1987, and JP-A-61/207,351.

SUMMARY OF THE INVENTION

Accordingly, a major object of the present invention is the provision of an improved process for the selective chlorination of phenolic compounds using gaseous chlorine, in a molten reaction medium and in the presence of an organic cation.

Briefly, the present invention features the selective chlorination, in the ortho position relative to the hydroxyl group, of phenolic compounds having the general formula (I):

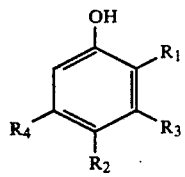

(I)

in which: $R_2$ is a halogen atom; an alkyl group having 1 to 4 carbon atoms; an alkoxy group having 1 to 4 carbon atoms; an acyloxy group having 2 to 4 carbon atoms; an acyl group having 2 to 4 carbon atoms; a carboxylic acid group; an ester group —$COOR_5$, wherein $R_5$ is a straight or branched chain alkyl radical having 1 to 4 carbon atoms; a nitrile group; an OH group; a —CHO group; an —$NO_2$ group; an acetamido group;

$R_1$ is a hydrogen atom or one of the substituents defined under $R_2$;

$R_3$ and $R_4$, which may be identical or different, are each a hydrogen atom or one of the substituents defined under $R_2$; and which comprises conducting said selective chlorination in a molten reaction medium, using gaseous chlorine, in the presence of a selectivity-enhancing effective amount of at least one organic cation.

DETAILED DESCRIPTION OF THE PREFERRED EMBODIMENTS OF THE INVENTION

More particularly according to the present invention, either a single organic cation or a mixture of several different organic cations can be employed.

By the term "organic cation", as utilized herein, are intended the onium ions deriving especially from nitrogen, phosphorus, arsenic, sulfur, selenium, oxygen, carbon or iodine and coordinated with hydrocarbon moieties. The onium ions deriving from nitrogen, phosphorus or arsenic will be tetracoordinated, the onium ions deriving from sulfur, selenium, oxygen, carbon or S═O will be tricoordinated, while the onium ions deriving from iodine will be dicoordinated.

The hydrocarbon moieties which are coordinated with these various elements are optionally substituted alkyl, alkenyl, aryl, cycloalkyl, aralkyl radicals, with the proviso that 2 coordinated hydrocarbon moieties may together form a single divalent radical.

The nature of the anions associated with these organic cations is not of critical importance. All of the "hard" or "borderline" bases are suitable as the anion.

The terms "hard" or "borderline" base connote any anion having the classical definition given by R. Pearson in *Journal of Chem. Ed.*, 45, pages 581–587 (1968).

Exemplary onium ions which can be used in the present chlorination process are those having the following general formulae:

(II)

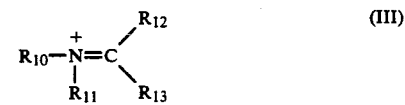

(III)

(IIIi)

(IV)

(V)

in which:

Z is N, P or As;

Y is S, 0, Se, S=O or C;

$R_6, R_7, R_8$ and $R_9$, which may be identical or different, are each a straight or branched chain alkyl radical having 1 to 16 carbon atoms and optionally substituted by one or more phenyl groups, hydroxyl groups, halogen atoms, nitro groups, alkoxy groups or alkoxycarbonyl groups, the alkoxy groups having 1 to 4 carbon atoms; a straight or branched chain alkenyl radical having 2 to 12 carbon atoms; an aryl radical having 6 to 10 carbon atoms and optionally substituted by one or more alkyl groups having 1 to 4 carbon atoms, alkoxy groups, alkoxycarbonyl groups, the alkoxy radical having 1 to 4 carbon atoms, or halogen atoms, with the proviso that two of said radicals $R_6$ to $R_9$ may together form a straight or branched chain alkylene, alkenylene or alkadienylene radical having 3 to 6 carbon atoms;

$R_{10}, R_{11}, R_{12}, R_{13}$, which may also be identical or different, are each a straight or branched chain alkyl radical containing 1 to 4 carbon atoms, with the proviso that the radicals $R_{12}$ and $R_{13}$ may together form an alkylene radical containing 3 to 6 carbon atoms, and the radicals $R_{11}$ and $R_{12}$ or $R_{11}$ and $R_{13}$ may together form an alkylene, alkenylene or alkadienylene radical containing 4 carbon atoms and, with the nitrogen atom, constitute a nitrogen-containing heterocycle;

$R_{14}$ is a divalent radical forming with the 2 nitrogen atoms a ring member having 4 to 6 atoms and optionally containing one or more nitrogen, sulfur and/or oxygen atoms, with the proviso that such heterocycle may be substituted by one or more radicals such as $R_6$.

Among the "hard" or "borderline" bases which can form the anion of said onium salts, representative are $F^-$, $ClO^-_4$, $PF^-_6$, $BF^-_4$, $SnCl^-_6$, $SbCl^-_6$, $B(Ph)^-_4$, $PO^{3-}_4$, $HPO^{2-}_4$, $H_2PO^-_4$, $CH_3SO^-_3$, $Ph-SO^-_3$, $HSO_4$, $NO_3$, $SO^{2-}_4$, $Cl^-$, $Br^-$, $I^-$, $OH^-$, with Ph denoting a phenyl radical, as well as all the other anions corresponding to Pearson's definition of a "hard" or "borderline" base.

For reasons of convenience of use, preferred such anions are: $PO^{3-}_4$, $HPO^{2-}_4$, $H_2PO^-_4$, $H_2PO^-_4$, $CH_3SO^-_3$ $Ph-SO^-_3$, $NO^-_3$, $SO^{2-}_4$, $PF^-_6$, $Cl^-$, $Br^-$, $I^-$, with Ph being defined as above. The anions $Cl^-$ and $Br^-$, and more especially the anion $Cl^-$, are advantageously used.

Exemplary of the organic cations corresponding to formula (II), representative are the cations:
tetramethylammonium,
triethylmethylammonium,
tributylmethylammonium,
trimethylpropylammonium,
tetraethylammonium,
tetrabutylammonium,
dodecyltrimethylammonium,
methyltrioctylammonium,
heptyltributylammonium,
tetrapropylammonium,
tetrapentylammonium,
tetrahexylammonium,
tetraheptylammonium,
tetraoctylammonium,
tetradecylammonium,
butyltripropylammonium,
methyltributylammonium,
pentyltributylammonium,
methyldiethylpropylammonium,
ethyldimethylpropylammonium,
tetradodecylammonium,
tetraoctadecylammonium,
hexadecyltrimethylammonium,
benzyltrimethylammonium,
benzyldimethylpropylammonium,
benzyldimethyloctylammonium,
benzyltributylammonium,
benzyltriethylammonium,
phenyltrimethylammonium,
benzyldimethyltetradecylammonium,
benzyldimethylhexadecylammonium,
dimethyldiphenylammonium,
methyltriphenylammonium,
2-butenyltriethylammonium,
N,N-dimethyltetramethyleneammonium,
N,N-diethyltetramethyleneammonium,
tetramethylphosphonium,
tetrabutylphosphonium,
ethyltrimethylphosphonium,
trimethylpentylphosphonium,
octyltrimethylphosphonium,
dodecyltrimethylphosphonium,
trimethylphenylphosphonium,
diethyldimethylphosphonium,
dioyclohexyldimethylphosphonium,
dimethyldiphenylphosphonium,
cyclohexyltrimethylphosphonium,
triethylmethylphosphonium,
methyltri(isopropyl)phosphonium,
methyltri(n-propyl)phosphonium,
methyltri(n-butyl)phosphonium,
methyltri(2-methylpropyl)phosphonium
methyltricyclohexylphosphonium,
methyltriphenylphosphonium,
methyltribenzylphosphonium,
methyltri(4-methylphenyl)phosphonium,
methyltrixylylphosphonium,
diethylmethylphenylphosphonium,
dibenzylmethylphenylphosphonium,
ethyltriphenylphosphonium,
tetraethylphosphonium,
ethyltri(n-propyl)phosphonium,
triethylpentylphosphonium,
hexadecyltributylphosphonium,
ethyltriphenylphosphonium,
n-butyltri(n-propyl)phosphonium,
butyltriphenylphosphonium,
benzyltriphenylphosphonium,
($\beta$-phenylethyl)dimethylphenylphosphonium,
tetraphenylphosphonium,
triphenyl(4-methylphenyl)phosphonium,
tetrakis(hydroxymethyl)phosphonium,
tetraphenylarsonium.

Exemplary of the cations corresponding to formulae (III) and (III'), representative are:
N-methylpyridinium,
N-ethylpyridinium,
N-hexadecylpyridinium,
N-methylpicolinium,
1,2,4-triphenyltriazolium.

Exemplary organic cations corresponding to formula (IV), representative are:
trimethylsulfonium,
triethylsulfonium,
triphenylsulfonium,
trimethylsulfoxonium,
triphenylcarbenium,
triethyloxonium, Exemplary organic cations corresponding to formula (V), representative are:
diphenyliodonium,
4,4'-dimethoxydiphenyliodonium (or the compounds described in *JACS*, 81, 342 (1958)),
diphenyliodonium-2-carboxylate.

Among the organic cations which are useful according to the process of the present invention, the quaternary ammonium ions, the quaternary phosphonium ions, the sulfonium ions and the iodonium ions will most typically be the preferred.

The amount of organic cation used in the process of this invention may vary over very wide limits.

It usually constitutes 0.005% to 25% by weight of onium salt relative to the weight of the phenolic compound (I). Preferably, amounts of organic cation will be used constituting 0.01% to 5% by weight of onium salt relative to the weight of the phenolic compound of formula (I).

The onium salt may be introduced in the solid state, or in the form of a solution in one of the solvents therefor, typically water.

The phenolic compounds of formula (I), for which the process of this invention is most applicable, are those of formula (I), in which:

(i) $R_2$ is:
a chlorine atom, a fluorine atom or a bromine atom;
a methyl, ethyl, propyl, isopropyl or tert-butyl group;
a methoxy or ethoxy group;
an aldehyde group;
an OH group;
a CN group;
an $NO_2$ group;
an acetoxy group;
an acetamido group;
an ester group $-COOR_5$, wherein $R_5$ is a methyl or ethyl group;
an acyl group having 2 to 4 carbon atoms;

(ii) $R_1$ is a hydrogen atom or has one of the definitions given for $R_2$;

(iii) $R_3$ and $R_4$ are:
one a hydrogen atom;
the other a hydrogen atom or a group such as defined under $R_2$.

As specific examples of phenolic compounds of the formula (I), especially representative are: 4-chlorophenol, 2,4-dichlorophenol, 3,4-dichlorophenol, 2-chloro-4-fluorophenol, 2,4-chloro-2-fluorophenol, 2-bromo-4-chlorophenol, 4-bromo-2-chlorophenol, 2-chloro-4-methoxyph 4-chloro-2-methoxyphenol, 4-chloro-2-methylphenol, 4-methoxyphenol, 4-ethoxyphenol, 4-hydroxyacetophe 4-hydroxybenzonitrile, 3-chloro-4-hydroxybenzaldehyde, 5-chloro-2-hydroxybenzaldehyde, 2-chloro-4-methylphenol, 2-chloro-4-tert-butylphenol, 2-chloro-4-nitrophenol, 4-chloro-2-nitrophenol, 4-nitrophenol, 2,4-dinitrophenol, 4-acetamido-2-chlorophenol, 2-acetamido-4-chlorophenol, 4-tert-butylphenol, 4-methylphenol, 4-ethylphenol, 4-isopropylphenol.

The process according to the present invention presents several advantages.

One of these advantages is in its intramolecular selectivity: when it is applied to a phenolic compound of formula (I) in which at least one of the meta positions relative to the hydroxyl group is free (unsubstituted), virtually only the ortho positions relative to the OH are chlorinated, while, in the absence of the organic cation, a not inconsiderable amount of the corresponding 3-chlorophenol or 5-chlorophenol is always formed, which is then very difficult to separate. Moreover, these compounds may be very troublesome for certain applications.

Another notable advantage concerns the intermolecular selectivity of the process: when the process is carried out using a mixture comprising a phenolic compound of formula (I) and one or more other phenolic compounds (such as, for example, position isomers of the said phenolic compound of formula (I)) which do not correspond to formula (I), it is largely the phenolic compound of formula (I) which is chlorinated, while the other phenolic compound or compounds are only slightly converted.

Thus, for example, the process of the invention may advantageously be applied to a mixture of 2,4-dichlorophenol and 2,6-dichlorophenol; 2,4,6-trichlorophenol is obtained from 2,4-dichlorophenol, while the 2,6-dichlorophenol, which is only slightly converted, may be separated relatively easily from the final reaction mixture.

It is also possible to use a crude industrial mixture containing 2,4-dichlorophenol, 2,6-dichlorophenol and 2,4,6-trichlorophenol and to thus obtain, as previously, 2,4,6-trichlorophenol and 2,6-dichlorophenol, which can be separated by fractional distillation.

Finally, another notable feature of the process of this invention resides in the fact that the reaction between the gaseous chlorine and the phenolic compound of formula (I) is virtually complete, while, in the absence of organic cation, a large portion of the chlorine does not react. The problems of recycling the excess chlorine or of treating the gaseous effluents thus become less difficult to avoid.

Consequently, the amount of chlorine used in the process of the invention is essentially a function of the desired rate of conversion of the phenolic compound (I).

The chlorine may be used alone or diluted with an inert gas, such as nitrogen for example The presence of an inert gas makes it possible, if required, to increase the gaseous flow rate without increasing the amount of chlorine introduced over a given time.

The temperature at which the process is carried out is generally less than or equal to 150° C. On the other hand, the lower limit of the temperature range is dependent upon the melting point of the phenolic compound (I) or of the mixture of phenolic compounds used.

This temperature generally ranges from the melting point of the reaction mixture to 120° C., but these values are not critical.

In order to further illustrate the present invention and the advantages thereof, the following specific examples are given, it being understood that same are intended only as illustrative and in nowise limitative.

EXAMPLES I TO 8:

The following charges:
(i) 2,4-dichlorophenol: 21.19 g (130 millimoles),
(ii) 2,6-dichlorophenol: 21.19 g (130 millimoles),
(iii) onium salt: nature and amount indicated in
the table hereinbelow, were introduced into a 250 cc glass reactor, provided with a paddle mixer, a tubing for the inlet of gaseous chlorine, and a thermometer, and with a condenser surmounted thereon which was connected to a column for destroying chlorine.

The temperature was adjusted to 70° C. under stirring in order to convert the mixture into a liquid state, and the introduction of gaseous chlorine was then begun at a flow rate of 5 liters/hour.

The duration of the chlorination carried out at 70° C. was 33 minutes, which corresponded to 2.76 liters of chlorine introduoed (123.millimoles). Hence, the test was carried out using a chlorine deficiency of 5% relative to the 2,4-dichlorophenol.

Upon completion of the reaction, the entire installation was flushed with a nitrogen stream. A reaction mass was obtained which was analyzed by gas chromatography in the presence of an internal standard.

The results obtained are reported in the following table.

TABLE

| TESTS | ONIUM SALT USED AS THE CATALYST | AMOUNT OF ONIUM SALT/2,4-DCP % W/W | CHLORINE (in moles) introduced | CHLORINE (in moles) fixed | CR % of 2,4-DCP | CR % of 2,6-DCP | YC % in 2,4,6-TCP | RATIO 2,4-DCP CR / 2,6-DCP CR |
|---|---|---|---|---|---|---|---|---|
| Control A | None | 0 | 0.123 | 0.107 | 47.2 | 38.6 | 99.9 | 1.2 |
| Example 1 | Tetrabutylammonium chloride | 0.5 | 0.123 | 0.112 | 76.5 | 14.5 | 100 | 5.3 |
| Example 2 | Benzyltrimethylhexadecyl-ammonium chloride | 0.75 | 0.123 | 0.121 | 85.4 | 12.0 | 100 | 7.1 |
| Example 3 | Tetraphenylphosphonium iodide | 0.5 | 0.123 | 0.119 | 54.9 | 23.9 | 99.5 | 2.3 |
| Example 4 | Methyltriphenylphophonium chloride | 0.5 | 0.123 | 0.115 | 76.2 | 19.1 | 98.2 | 4.0 |
| Example 5 | Tetrabutylphosphonium bromide | 0.5 | 0.123 | 0.119 | 80.7 | 13.4 | 98.4 | 6.0 |
| Example 6 | Tetraphenylarsonium chloride | 0.5 | 0.123 | 0.119 | 71.1 | 26.1 | 94.5 | 2.7 |
| Example 7 | Diphenyliodonium chloride | 0.5 | 0.123 | 0.120 | 87.6 | 7.5 | 97.1 | 11.7 |
| Example 8 | Triphenylsulphonium chloride (50% W/W aqueous solution) | 0.5 | 0.123 | 0.119 | 76.2 | 19.3 | 98.9 | 3.9 |

% W/W = weight by weight percentage
CR = coversion rate
2,4-DCP = 2,4-dichlorophenol
2,6-DCP = 2,6-dichlorophenol
YC = yield relative to the converted dichlorophenol
2,4,6-TCP = 2,4,6-trichlorophenol

EXAMPLE 9

(i) 2,4-dichlorophenol: 32.6 g (200 millimoles),
(ii) tetrabutylammonium chloride: 0.3 g (about 1% by weight relative to the dichlorophenol),
were introduced into the apparatus described in Examples 1 to 8.

The mixture was heated to 70° C. under stirring, in order to convert it to the liquid state, and gaseous chlorine was then introduced at a flow rate of 5 liters/hour.

The duration of the chlorination carried out at 70° C. was 54 min, which corresponded to the introduction of 200 millimoles of chlorine.

The test was carried out as indicated in Examples 1 to 8. A control test B was carried out under the same conditions, but without tetrabutylammonium chloride. In order to have a sufficient conversion rate (CR) of the 2,4-dichlorophenol, it was necessary to introduce an excess of chlorine of about 60%, relative to the stoichiometric amount.

The following results were obtained:

EXAMPLE 9

CR of 2,4-dichlorophenol: 100%
YC of 2,4,6-trichlorophenol: 99.3%

Control B

CR of 2,6-dichlorophenol: 85.0%
YC of 2,4,6-trichlorophenol: 97.0%

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the selective chlorination, in the ortho position relative to the hydroxyl group, of a phenolic compound having the formula (I):

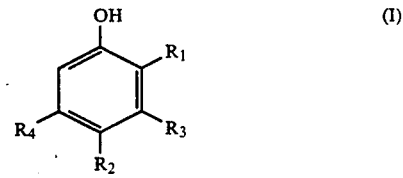

in which:
R$_2$ is a halogen atom; an alkyl group having 1 to 4 carbon atoms; an alkoxy group having 1 to 4 carbon atoms; an acyloxy group having 2 to 4 carbon atoms; an alkanoyl acyl group having 2 to 4 carbon atoms; a carboxylic acid group; an ester group —COOR$_5$, wherein R$_5$ is a straight or branched alkyl radical having 1 to 4 carbon atoms; a nitrile group; an OH group; a —CHO group; an —NO$_2$ group; an acetamideo group;
R$_1$ is a hydrogen atom or a substituent R$_2$;
R$_3$ and R$_4$, which may be identical or different, are each a hydrogen tom or a substituent R$_2$; comprising conducting said selective chlorination in a molten medium, using gaseous chlorine, in the presence of a selectivity-enhancing effective amount of at least one organic cation comprising an onium ion derived from nitrogen, phosphorus, arsenic, sulfur, selenium, oxygen, carbon or iodine and which is coordinated with a hydrocarbon moiety.

2. The process as defined by claim 1, carried out in the presence of said at least one organic cation of an onium salt, said organic cation having one of the following formulae:

-continued

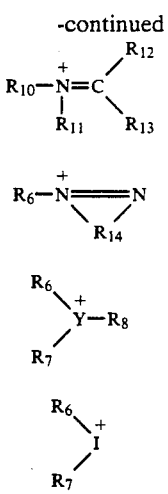

(III)

(IIIi)

(IV)

(V)

in which:

Z is N, P or As;

Y is S, O, Se, S=O or C;

$R_6, R_7, R_8$ and $R_9$, which may be identical or different, are each a straight or branched chain alkyl radical having 1 to 16 carbon atoms and optionally substituted by one or more phenyl groups, hydroxyl groups, halogen atoms, nitro groups, alkoxy groups or alkoxycarbonyl groups, the alkoxy groups having 1 to 4 carbon atoms; a straight or branched chain alkenyl radical having 2 to 12 carbon atoms; a carbocyclic an aryl radical having 6 to 10 carbon atoms and optionally substituted by one or more alkyl groups having 1 to 4 carbon atoms, alkoxy groups, alkoxycarbonyl groups, the alkoxy radical having 1 to 4 carbon atoms, or halogen atoms, with the proviso that two of said radicals $R_6$ to $R_9$ may together form a straight or branched chain alkylene, alkenylene or alkadienylene radical having 3 to 6 carbon atoms;

$R_{10}$, R hd 1, $R_{12}$, $R_{13}$, which may also be identical or different, are each a straight or branched chain alkyl radical containing 1 to 4 carbon atoms, with the proviso that the radicals $R_{12}$ and $R_{13}$ may together form an alkylene radical containing 3 to 6 carbon atoms, and the radicals $R_{11}$ and $R_{12}$ or $R_{11}$ and $R_{13}$ may together form an alkylene, alkenylene or alkadienylene radical containing 4 carbon atoms and, with the nitrogen atom, constitute a nitrogen-containing heterocycle;

$R_{14}$ is a divalent radical forming with the two nitrogen atoms a ring member having 4 to 6 atoms and optionally containing one or more nitrogen, sulfur and/or oxygen atoms, with the proviso that such heterocycle may be substituted by one or more radicals $R_6$.

3. The process as defined by claim 2, wherein the anion associated with said at least oen organic cation comprises $F^-$, $ClO^-_4$, $PF^-_6$, $BF^-_4$, $SnCl^-_6$, $SbCl^-_6$, $B(Ph)^-_4$, $PO^{3-}_4$, $HPO^{2-}_4$, $H_2PO^-_4$, $CH_3SO^-_3$, $Ph-SO^-_3$, $HSO^-_4$, $NO^-_3$, $SO^{2-}_4$, $Cl^-$, $Br^-$, $I^-$ or $OH^-$, with Ph denoting a phenyl radical.

4. The process as defined by claim 3, said anion comprising $PO^{3-}_4$, $HPO^{2-}_4$, $H_2PO^-_4$, $CH_3SO^-_3$, $Ph-SO^-_3$, $HSO^-_4$, $NO^-_3$, $SO^{2-}_4$, $SO^{2-}_4$, $PF^-_6$, $Cl^-$, $Br^-$ or $I^-$, with Ph denoting a phenyl radical.

5. The process as defined by claim 2, said at least one organic cation comprising a quaternary ammonium, quaternary phosphonium, sulfonium or iodonium oation.

6. The process as defined by claim 2, wherein the organic cation is present in such an amount that the weight of the onium salt relative to the weight of the phenolic compound of formula (I) ranges from 0.005% to 25%.

7. The process as defined by claim 6, wherein the organic cation is present in such an amount that the weight of the onium salt relative to the weight of the phenolic compound of formula (I) ranges from 0.01 to 5%.

8. The process as defined in claim 1, wherein the phenolic compound having the formula (I):

$R_2$ is a chlorine atom, a fluorine atom or a bromine atom; a methyl, ethyl, propyl, isopropyl or tert-butyl group; a methoxy or ethoxy group; an aldehyde group; an OH group; a CM group; an $NO_2$ group; an acetoxy group, an acetimido group; an ester group $-COOR_5$, wherein $R_5$ is a methyl or ethyl group; an alkanoyl acyl group having 2 to 4 carbon atoms;

$R_1$ is a hydrogen atom or a substituent $R_2$;

$R_3$ and $R_4$ are:

one a hydrogen atom;

the other a hydrogen atom or a substituent $R_2$.

9. The process as defined by claim 1, said phenolic compound having the general formula (I) comprising -chlorophenol, 2,4-dichlorophenol, 3,4-dichlorophenol, -chloro-4-fluorophenol, 4-chloro-2-fluorophenol, 2-bromo-4-chlorophenol, 4-bromo-2-chlorophenol, 2-chloro-4-methoxyphenol, 4-chloro-2-methoxyphenol, 4-chloro-2-methylphenol, 4-methoxyphenol, 4-ethoxyphenol, 4-hydroxyacetophenone, 4-hydroxybenzonitrile, 3-chloro-4-hydroxybenzaldehyde, 5-chloro-2-hydroxybenzaldehyde, 2-chloro-4-methylphenol, 2-chloro-4-tert-butylphenol, 2-chloro-4-nitrophenol, 4-nitrophenol, 2,4 dinitrophenol, 2-acetamido-4-chlorophenol, 4-acetamido-2-chlorophenol 4-tert-butylphenol, 4-methylphenol, 4-ethylphenol or 4-isopropylphenoi.

10. The process as defined by claim 1, said phenolic compound having the general formula (I) comprising admixture of 2,4-dichlorophenol and 2,6-dichlorophenol.

11. The process as defined by claim 1, said phenolic compound having the general formula (I) comprising admixture of 2,4-dichlorophenol, 2,6-dichlorophenol and 2,4,6-trichlorophenol.

12. The process as defined by claim 1, carried out at a temperature less than or equal to 150 C.

13. The process as defined by claim 12, said temperature ranging from the melting point of the reaction mixture to 120° C.

* * * * *